United States Patent [19]
Alvarez

[11] Patent Number: 4,875,473
[45] Date of Patent: Oct. 24, 1989

[54] MULTI-LAYER WOUND DRESSING HAVING OXYGEN PERMEABLE AND OXYGEN IMPERMEABLE LAYERS

[75] Inventor: Oscar M. Alvarez, East Brunswick, N.J.

[73] Assignee: Bioderm, Inc., N.J.

[21] Appl. No.: 847,934

[22] Filed: Apr. 3, 1986

[51] Int. Cl.$^4$ .................. A61F 13/00; A61F 15/00
[52] U.S. Cl. .................. 128/155; 128/156; 604/307; 428/424.6
[58] Field of Search .......... 128/156, 155; 604/369, 604/304, 307, 389; 428/216, 424.6, 424.8

[56] References Cited

U.S. PATENT DOCUMENTS

| | | | |
|---|---|---|---|
| 1,920,808 | 8/1933 | Sander | 128/156 |
| 2,273,873 | 2/1942 | Klein | 128/156 |
| 2,969,144 | 1/1961 | Zackheim | 128/156 |
| 4,064,296 | 12/1977 | Bornstein et al. | 428/516 |
| 4,287,251 | 9/1981 | King | 128/156 |
| 4,292,299 | 9/1981 | Suzuki | 128/156 |
| 4,341,208 | 7/1982 | Gordon | 128/156 |
| 4,414,970 | 11/1983 | Berry | 128/156 |
| 4,499,896 | 2/1985 | Heinecke | |
| 4,556,441 | 12/1985 | Faasse, Jr. | 128/156 |
| 4,561,435 | 12/1985 | McKnight et al. | |
| 4,600,001 | 7/1986 | Gilman | 128/156 |

OTHER PUBLICATIONS

Oscar M. Alvarez, et al. Healing Wounds: Occlusion or Exposure, Infection in Surgery, pp. 173-181, Mar. 1984.
Oscar M. Alvarez, et al. The Effect of Occlusive Dressings on Collagen Synthesis and Re-epithelialization in Superficial Wounds, Journal of Surgical Research 35, 142-148 (1983).
David R. Knighton, et al. Regulation of Repair: Hypoxic Control of Macrophage Mediated Angiogenesis, pp. 41-49.

Primary Examiner—Richard J. Apley
Assistant Examiner—Paul Prebilic
Attorney, Agent, or Firm—Brumbaugh, Graves, Donohue & Raymond

[57] ABSTRACT

A multi-layer wound dressing is provided which facilitates wound healing by creating hypoxia followed, after 3 to 72 hours, by an aerobic environment. The dressing is made of (a) a low-oxygen permeability outer layer; (b) an oxygen permeable inner layer, affixed on one side to the outer layer; and (c) an adhesive applied to the other side of the inner layer. The adhesive may be applied in a continuous or discontinuous manner, and may be applied only around the perimeter of the dressing, leaving an adhesive-free window. The entire dressing is applied to the wound and creates a hypoxic environment until the outer low oxygen permeability layer is removed after 3 to 72 hours. The oxygen permeable layer is left on to provide protection during a subsequent aerobic healing phase.

9 Claims, 1 Drawing Sheet

MULTI-LAYER WOUND DRESSING HAVING OXYGEN PERMEABLE AND OXYGEN IMPERMEABLE LAYERS

BACKGROUND OF THE INVENTION

The present invention relates to a multi-layer dressing for wounds which provides for an initial period of wound hypoxia followed by oxygen availability to the wound, without disturbing the covering immediately in contact with the wound.

As understanding of the healing process has progressed, various theories have been advanced on the most advantageous way to treat wounds to promote healing. For many years, it was generally believed the wounds required atmospheric oxygen to aid epithelial resurfacing and so oxygen permeable wound dressings were used. Subsequently, however, it has been reported that oxygen-free or hypoxic conditions are either as good as, or preferable to aerobic conditions for the promotion of healing.

Alvarez et al. compared the effects of oxygen permeable and oxygen impermeable occlusive dressings on collagen synthesis and re-epithelialization. *Infections in Surgery*, March, 1984, pages 173-181. They found that occlusive dressings, and not the presence or absence of oxygen, led to improvement in both collagen synthesis and re-epithelialization.

Knighton et al. have reported that macrophage mediated angiogenesis is promoted by hypoxic conditions, and that, at least to the extent that new capillary growth is required, hypoxia is preferably maintained throughout most of the healing process. Allowing oxygen to contact the wound was found to slow angiogenesis unless capillary regeneration had proceeded to a point where more than 80% of the wound space had been filed. In that case, angiogenesis proceeded at the same rate, regardless of the atmospheric oxygen tension within the wound.

SUMMARY OF THE INVENTION

It has now been found that for wounds, particularly wounds requiring debridement, optimum healing results if a wound is first covered with an oxygen impermeable dressing to promote hypoxia, and subsequently allowed contact with atmospheric oxygen. Depending on the nature and extent of the wound, periods of hypoxia from about 3 to about 72 hours are indicated.

Such treatment is provided according to this invention by the application of a multi-layer wound dressing. The dressing is made of (a) an outer layer of a material having low-oxygen permeability;

(b) an inner layer of a highly oxygen permeable material, affixed on one side to the outer layer; and (c) an adhesive applied to at least a part of the other side of the inner layer. The adhesion between the inner layer and the skin is greater than the adhesion between the inner and outer layers

DETAILED DESCRIPTION OF THE INVENTION

When wounding occurs, disruption in blood flow to the wound site leads to an initial decrease in the oxygen supply to cells at the wound surface. Inadequate blood supply and oxygen consumption leads to a state of localized hypoxia and cells in the hypoxic region shift from an aerobic to an anaerobic metabolism. As a part of this shift, enzymes which are not ordinarily present or active in aerobic tissue are synthesized and activated. It now appears that one of these enzymes plays a significant role in triggering the healing Lactate dehydrogenase (LDH) is produced in response to hypoxia to catalyze the conversion of pyruvic acid to lactic acid, providing energy to cells existing in an anerobic environment. Lactic acid accumulates until the anaerobic condition is terminated and then is reconverted to pyruvic acid by LDH. I believe that LDH acts as a triggering mechanism for the healing process. Induction of increase amounts of LDH should, therefore, lead to more rapid triggering. Prolonged hypoxia would not be required, however, since LDH does not immediately disappear following the return of oxygenation.

Consistent with this theory, it has been found that wounds which are initially covered with an oxygen impermeable dressing which enhances and prolongs hypoxia, and then subsequently covered with an oxygen permeable dressing exhibit improved rates of epidermal resurfacing as compared to wounds treated with either oxygen permeable or oxygen impermeable dressings alone. Furthermore, it has been found that epidermal cells grown in culture exhibit maximum adherence at 13 mm Hg. of oxygen, but undergo maximum regeneration at 37 mm of Hg. Fibroblasts exhibit maximum growth at about 16 mm Hg.

Superficial partial thickness wounds (epidermal and inclusive of papillary dermis) can be effectively treated with as little as 6 hours of hypoxia, while wounds requiring substantial debridement should be treated for up to 72 hours. In general, however, the preferred duration for the hypoxic phase of the treatment is about 24 hours. Maintaining hypoxia for periods in excess of 72 hours may not lead to an enhancement of healing, and may result in detrimental effects such as anaerobic organism overgrowth or shifts in microbial flora. Although not a direct effect of hypoxia, prolonged use of the dressing according to this inventions can also lead to tissue maceration due to poor transmission of moisture vapor when both films are intact.

Figure 1:
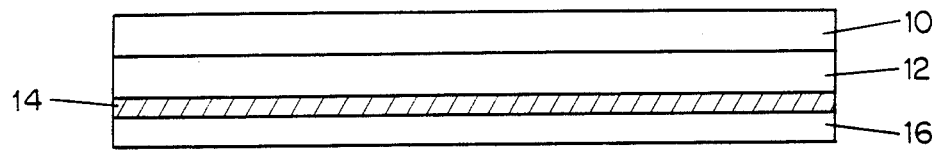
FIG. 1 is a cross-sectional view of a multi-layer wound dressing.

Advantageous treatment of wounds to promote healing can be achieved utilizing a multi-layer wound dressing. As shown in FIG. 1, the multi-layer dressing comprises an oxygen impermeable outer layer (10) affixed to one side of an oxygen permeable inner layer (12). Inner layer (12) has a coating of adhesive (14) applied to all or part of the other side of inner layer (12). Prior to application, adhesive (14) is protected by a layer of a release sheet (16) which is removed to expose the adhesive for application of the dressing to the wound area.

The outer layer of the dressing may be made of any material with low-oxygen permeability which can be formed into a continuous film of sufficient flexibility for use as a wound dressing. Preferably, the outer layer should have an oxygen permeability of less than about 200 cm$^3$/100 in$^2$/mil/24 hrs. In particular, films of polyvinyl alcohol, polyviriylidene chloride, polyvinyl chloride, high density polyethylene and high density polypropylene are suitable for use as the outer layer of the multi-layer dressing.

The inner layer of the dressing may be made of any oxygen permeable material which can be formed into a continuous film of sufficient flexibility for use as a wound dressing. Suitable materials include films made of polyurethane, co-polyester, mixtures of polyester and urethanes, foams, and silicone materials.

If desired, either or both of the layers can be opacified and colored to blend in with skin coloration.

In the assembled dressing, the inner and outer layers are affixed together. This can be achieved using an attraction based on static charge. As an alternative, a low-tack adhesive may be used. The use of a low-tack adhesive permits the low-oxygen permeability outer layer to be re-affixed to the inner layer if it is removed prematurely.

The adhesive applied to the inner side of the oxygen permeable layer is used to attach the dressing to the patient's skin. It will be understood that any suitable nontoxic adhesive for use in bandages or dressings can be used for this purpose. Preferably, the adhesive will be a pressure sensitive adhesive. Suitable adhesives include ether based or water based adhesives, acrylates, polyisobutylene, starch based adhesives, pectin, and other hydrocolloids or gums. Adhesive preparations having antimicrobial effects, or those containing medications are also suitable for use in this invention.

The adhesive is applied to all or part of the surface of the inner layer. This means that the adhesive can be applied in a continuous fashion. The adhesive can also be restricted to the margins of the dressing so that an adhesive-free window remains in the central portion of the dressing which will be in actual contact with the wound.

As is conventionally known, a layer of release material may be used to cover the adhesive until the time of application of the dressing.

Figure 2:
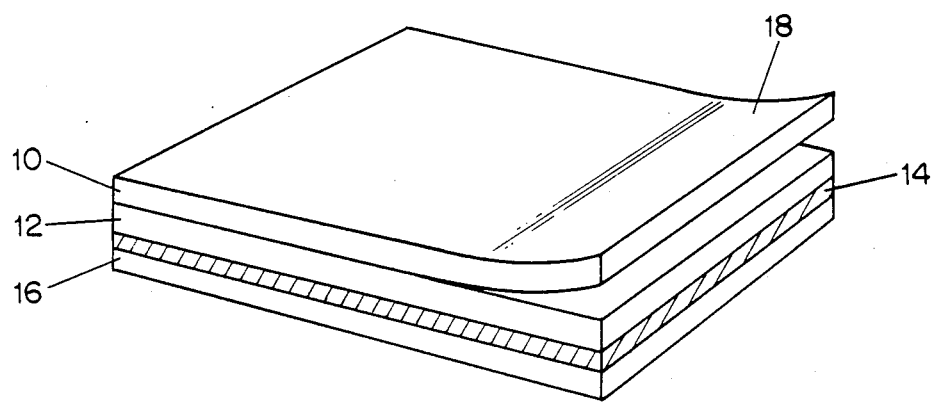
FIG. 2 shows a three-dimensional projection of a multi-layer wound dressing.

A preferred embodiment of the multi-layer wound dressing according to this invention is shown in FIG. 2. The dressing is made of outer layer (10), inner layer (12), and adhesive (14) and a release sheet (16). In addition, a tab (18) is attached along one edge of outer layer (10). The tab (18) does not adhere to inner layer (12), and serves to allow easy removal of the outer layer. Preferably, tab (18) is made of a material which is readily marked with conventional writing implements.

This will allow the treating professional to write instructions for the removal of outer layer (10) directly on the dressing.

Optionally, a second tab may be included along the opposite edge of the dressing. This tab would be brightly colored, e.g. red, or obviously numbered to alert the patient that the dressing still needs attention.

As a further refinement, the dressings according to the claimed invention may include a removable coding strip which can be used for billing and inventory control purposes, and to monitor the occurrence of treatments in hospital. Advantageously, the coding strip is an adhesive backed perforated extension of the wound dressing which is separated from the dressing and adhered to the patient's chart at the time of application of the dressing. The coding strip preferably has printed upon it the type and inventory control numbers of the dressing in both conventional and machine readable formats, and may advantageously be made of a material which is readily marked with conventional writing implements to allow for noting the date or time of application on the coding strip.

It will be understood by one skilled in the art that the low-oxygen permeability outer layer of a multi-layer wound dressing according to this invention may be smaller in area than the oxygen permeable inner layer. If this is the case, the low-oxygen permeability layer should be centered over the wound, and sized such that it completely covers the wound area.

EXAMPLE

The effect of oxygen impermeable (low permeability) and oxygen permeable films and of multi-layer dressings according to this invention on epidermal resurfacing of partial thickness wounds was studied. Pigs were wounded to a depth of 0.3 mm, and the wounds treated according to one of the following regimens: (1) untreated; (2) polyurethane film; (3) co-polyester film; (4) polyethylene film; (5) polyvinylidene film; (6) polypropylene film; (7) multi-layer dressing of polypropylene and co-polyester films; and (8) multi-layer dressing of polypropylene and polyurethane films. Each of the dressings was affixed with an adhesive applied only to the perimeter of the dressing such that the wound was not contacted with the adhesive.

From day 2 through day 6 after wounding, wounds from each treatment regimen were evaluated to determine the extent of epidermal resurfacing. From these results, $HT_{50}$, the time required for 50% of the wounds to be 100% healed was determined for each treatment regimen. The values of $HT_{50}$ in Table 1 clearly show that treatment with multi-layer dressings according to this invention is superior to single dressings of either oxygen permeable or oxygen impermeable material.

TABLE 1

| TREATMENT | $HT_{50}$ (DAYS)[a] | RELATIVE RATE OF HEALING[b] COMPARED TO UNTREATED (%) |
|---|---|---|
| UNTREATED | 4.1 | — |
| POLYPROPYLENE/POLYURETHANE | 2.8 | +31 |
| POLYPROPYLENE FILM | 3.2 | +22 |
| POLYVINYLIDENE FILM | 3.1 | +22 |
| POLYETHYLENE FILM | 3.1 | +24 |
| CO-POLYESTER | 3.4 | +17 |
| POLYURETHANE FILM | 3.4 | +17 |
| POLYPROPYLENE/CO-POLYESTER | 2.8 | +31 |

[a] $HT_{50}$ = Healing time 50, days needed for 50% of wounds to be 100% healed.
[b] Relative rate of healing = (untreated $HT_{50}$)/untreated $HT_{50}$ × 100.

I claim:
1. A multi-layer wound dressing comprising:
   (a) an outer layer of a continuous film material having low-oxygen permeability and capable of creating a hypoxic environment thereunder;
   (b) an inner layer of an oxygen permeable continuous film material sized to entirely cover a wound said outer layer being affixed to one side of the inner layer; and (c) an adhesive applied to at least a part of the other side of the inner layer, said adhesive being such that when the dressing is applied the adhesion of the inner layer to skin is greater than the adhesion of the inner layer to the outer layer.

2. A dressing according to claim 1, wherein the outer layer has an oxygen permeability less than about 200 $cm^3/100\ in^2/mil\ 4\ hrs$.

3. A dressing according to claim 1, wherein the low-oxygen permeability material is selected from the group consisting of polyvinyl alcohol, polyvinylidene chloride, polyvinylchloride, high density polyethylene, and high density polypropylene.

4. A dressing according to claim 3, wherein the oxygen permeable material is selected from the group consisting of polyurethane and co-polyester.

5. A dressing according to claim 4, wherein the adhesive is a pressure sensitive adhesive.

6. A dressing according to claim 4, wherein the adhesive is applied only around the margin of the inner layer such that an adhesive-free window is present in a center portion of the dressing.

7. A dressing according to claim 5, wherein the outer layer is affixed to the inner layer with a low tack adhesive.

8. A dressing according to claim 1, further comprising a tab affixed to one edge cf the outer layer, said tab being unattached to the inner layer such that removal of the outer layer is facilitated.

9. A dressing according to claim 8, wherein the tab is made of a material which car be written upon using conventional writing implements such that instructions for removal of the outer layer can be written thereon.

* * * * *